United States Patent [19]

Hattori

[11] Patent Number: 4,612,708
[45] Date of Patent: Sep. 23, 1986

[54] REPLACEABLE BLADE TYPE MEDICAL SCISSORS

[76] Inventor: Katsura Hattori, 1-13, Eikin-cho, Syouwa-ku, Nagoya-City, Aichi-Prefecture, Japan

[21] Appl. No.: 711,015

[22] Filed: Mar. 12, 1985

[30] Foreign Application Priority Data

Mar. 15, 1984 [JP] Japan .................. 59-37921[U]

[51] Int. Cl.$^4$ .................................................. B26B 13/04
[52] U.S. Cl. ...................................................... 30/260
[58] Field of Search ..................... 30/260, 341, 349

[56] References Cited

U.S. PATENT DOCUMENTS

| 468,207 | 2/1892 | Prohaska | 30/260 |
| 995,090 | 6/1911 | Piper | 30/260 |
| 1,556,770 | 10/1925 | Driest | 30/260 |
| 1,645,035 | 10/1927 | Zeidler | 30/260 |
| 1,783,853 | 12/1930 | Miriello | 30/260 |
| 1,884,630 | 10/1932 | Driest et al. | 30/260 |
| 4,062,113 | 12/1977 | Ishida et al. | 30/260 |

Primary Examiner—Jimmy C. Peters

Attorney, Agent, or Firm—Wenderoth, Lind & Ponack

[57] ABSTRACT

Replaceable blade type medical scissors are composed of scissor bodies and replaceable blades. Each of the replaceable blades is composed of a blade portion made of a metal plate which is bent such as to have an arcuate cross section and a retaining portion which is constructed by the metal plate bent into an envelope form which gradually increases in width towards the base portion. Each replaceable blade is adapted to allow plastic deformation and is integrally provided at the base portion of the blade portion. An insertion piece which is provided at the end portion of the scissor body is inserted into the retaining portion of the replaceable blade while the retaining portion is slightly expanded. The replaceable blade is removably secured to the scissor body by the elastic contracting force of the retaining portion. This structure dispenses with the troublesome task of sterilization and re-assembly and makes the scissor bodies interchangeable by a simple operation of mounting on the scissors appropriately selected blades in accordance with the intended use from among various kinds of replaceable blades prepared in advance.

1 Claim, 13 Drawing Figures

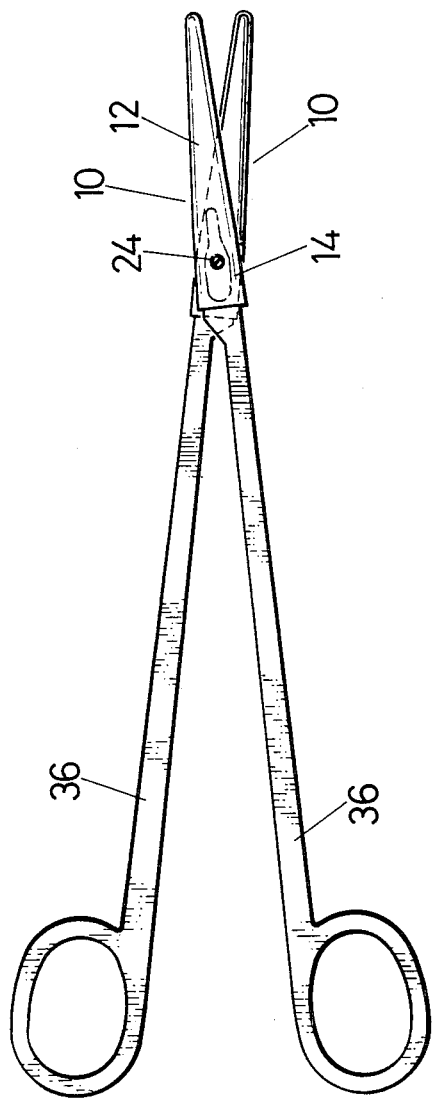
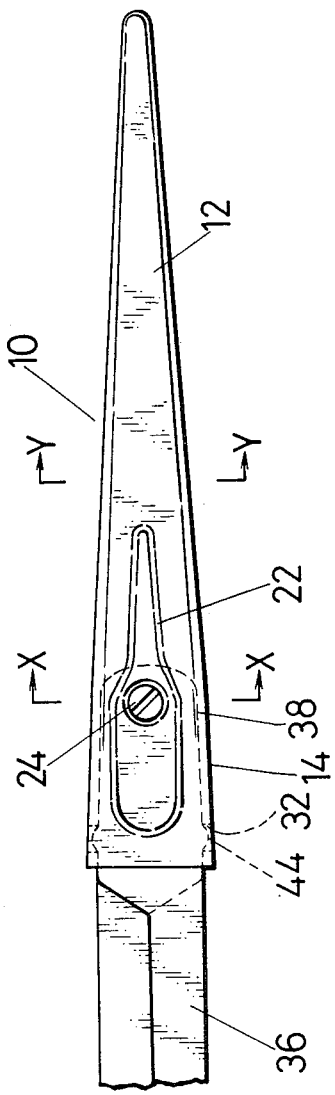
FIG. 1
FIG. 2

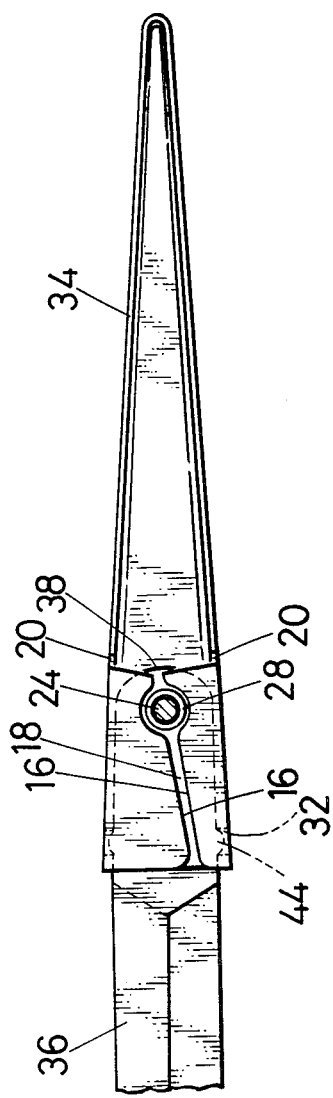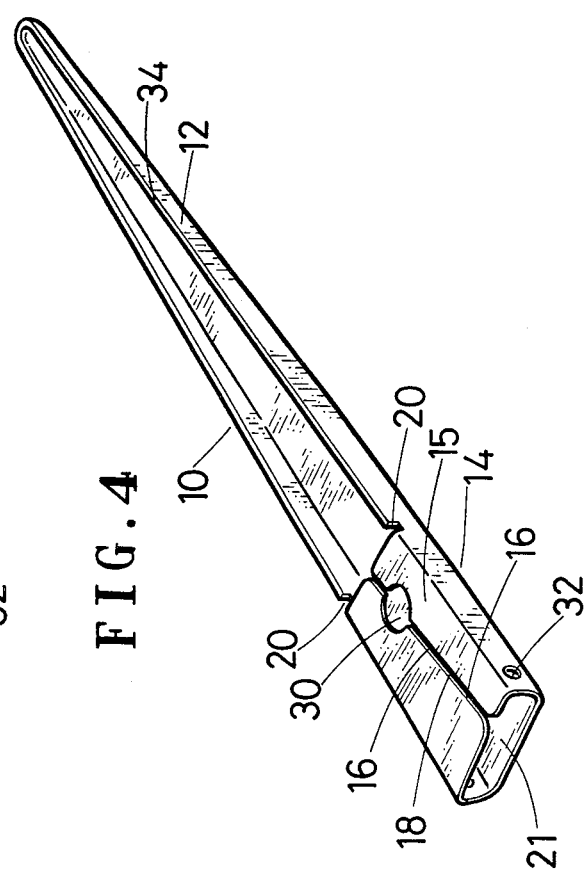

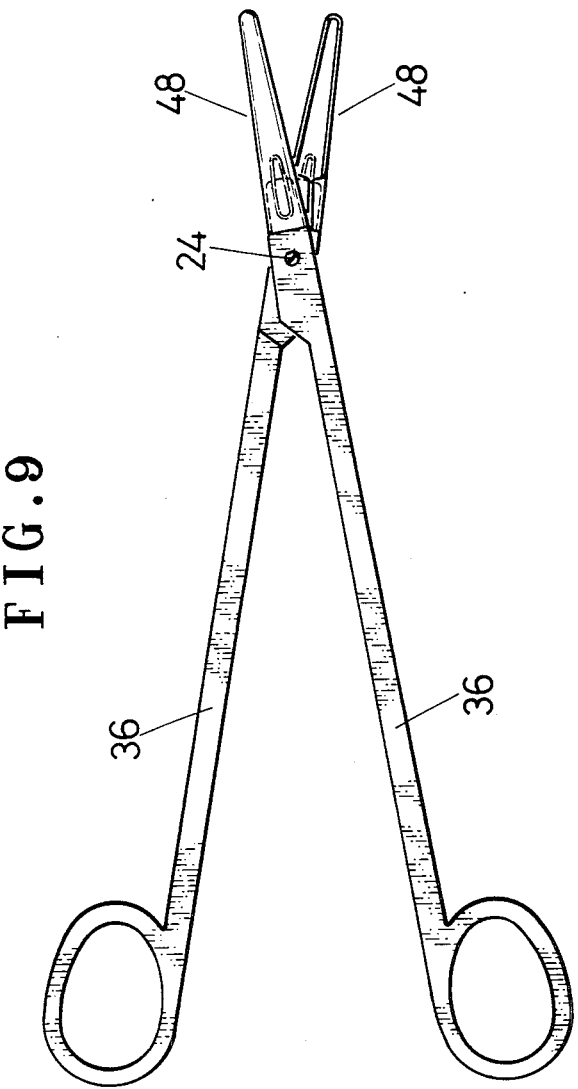
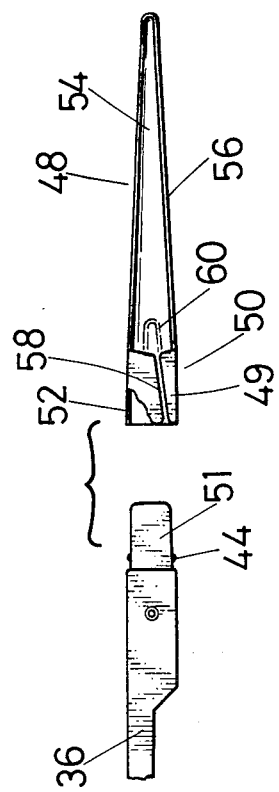
FIG. 9
FIG. 10

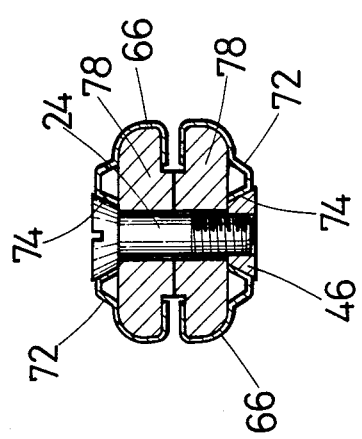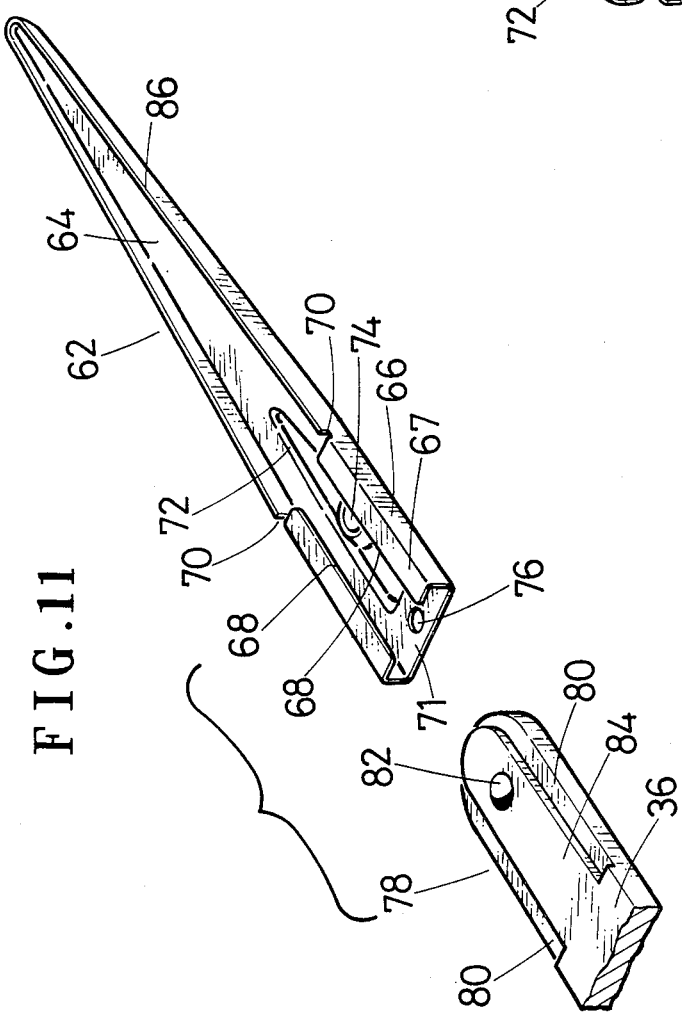

REPLACEABLE BLADE TYPE MEDICAL SCISSORS

FIELD OF THE INVENTION

This invention relates to a type of medical scissors in which the blade portions are replaceable.

DESCRIPTION OF THE PRIOR ART

The conventional medical scissors, as is shown in FIG. 13, have the same structure as ordinary scissors in which scissor bodies 102 and blade portions 104 are made integral. It is, therefore, necessary to disassemble and sterilize with hot water each scissor member after use. This is extremely troublesome because each operation of disassembly, sterilization and reassembly must be frequently conducted with respect to medical scissors.

At the time of reassembly, if a scissor member is mismatched with the member of another pair, the cutting quality of the scissors is remarkably deteriorated. Accordingly it is inconveniently necessary to identify pairs correctly and for this purpose a stamp 106 is impressed on each scissor member to serve as a guide to the user.

In addition, when these conventional medical scissors are used, a number of kinds of scissors having blade portions 104 of different sizes and shapes must be prepared, depending upon the intended uses. Therefore, the number of pairs which need to be prepared is large and, hence, dealing with them is a very troublesome task.

SUMMARY OF THE INVENTION

This invention provides a type of medical scissors having replaceable blades each of which is composed of a blade portion made of a metal plate which is bent in the widthwise direction such that its lateral edges are at right angles to its surface each blade portion also has a retaining portion which is constructed by the metal plate bent into an envelope form which gradually increases in width towards the base portion. Each replaceable blade is adapted to allow plastic deformation and is integrally provided at the base portion of the blade portion. An insertion plate portion which is provided at the end portion of the scissor body is inserted on to the retaining portion of the replaceable blade while the retaining portion is slightly expanded, and this insertion plate portion removably secures the replaceable blade to the scissor body by the contracting force of its own elasticity.

It is an object of the invention to dispense with any need for sterilization and reassembly which have been thought troublesome, by providing replaceable blades at the blade portions in a pair of medical scissors.

It is another object of the invention to make a scissor body suitable for any use by providing a selection of various kinds of replaceable blades prepared in advance for requisite uses and adapting the scissor body for mounting a selected blade appropriate to a given use.

The above and other objects, features and advantages of the present invention will become clear from the following description of the preferred embodiments thereof, taken in conjunction with the accompanying drawings.

BRIEF DESCRIPTION OF THE DRAWINGS

FIG. 1 is a plan view of a first embodiment of replaceable blade type medical scissors according to the invention;

FIG. 2 is an enlarged plan view of a replaceable blade 10 of the first embodiment shown in FIG. 1;

FIG. 3 is an enlarged rear elevational view of the replaceable blade 10;

FIG. 4 is a perspective view of the replaceable blade 10;

FIG. 9 is a plan view of a second embodiment of replaceable blade type medical scissors according to the invention;

FIG. 10 is a plan view of a replaceable blade 48, the scissor body 36 and an insertion piece 51 of the second embodiment;

FIG. 11 is a perspective view of a replaceable blade 62, the scissor body 36 and an insertion piece 78 of a third embodiment of replaceable blade type medical scissors according to the invention;

FIG. 12 is an enlarged sectional view of a connecting pin 24; and

DETAILED DESCRIPTION OF THE PREFERRED EMBODIMENTS

FIGS. 1 to 8 show a first embodiment of the invention.

Figure 7:
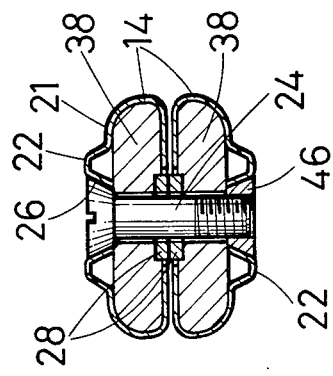
FIG. 7 is an enlarged sectional view taken along the line X—X of FIG. 2.
Figure 13:
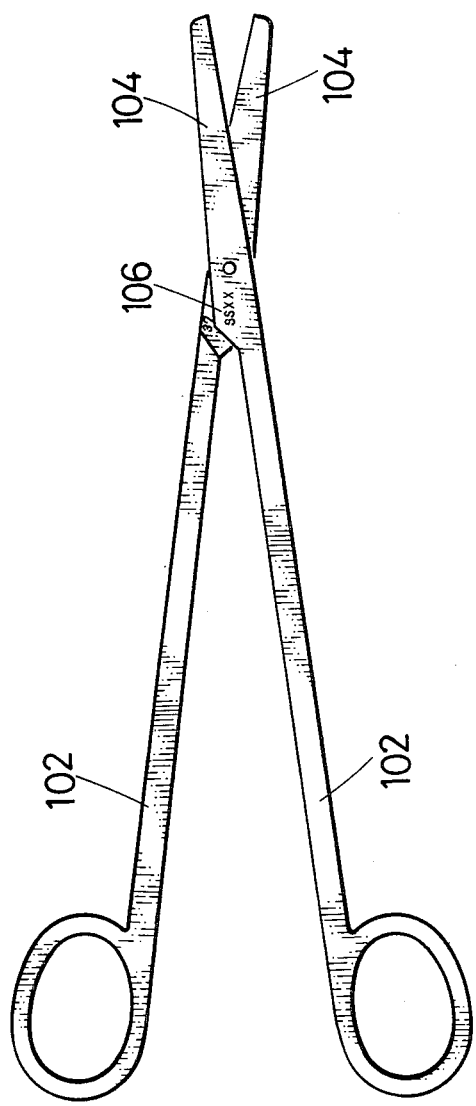
FIG. 13 is a plan view of the conventional prior art medical scissors.

In the first embodiment of replaceable blade type medical scissors, a connecting pin is provided on the retaining portion of the replaceable blades. In FIGS. 1 and 2, a replaceable blade 10 is composed of a blade portion 12 made of a metal plate bent in such a manner as to have an arcuate cross section. A retaining portion 14 is made of the metal plate bent into an envelope shape such as to allow plastic deformation and is integrally provided at the base portion of the blade portion 12. The blade portion 12 gradually tapers in width toward the narrow end portion. The retaining portion 14 also has a tapered shape with a larger width at its distal end portion. As shown in FIGS. 3 and 4, edges 16 of the metal plate situated on the facing surface 15 of the retaining portion 14 oppose each other with a narrow space 18 between them, and are slightly inclined in the lengthwise direction of the replaceable blade 10. Notches 20 are formed at the portion connecting the blade portion 12 and the retaining portion 14 to facilitate plastic deformation of the retaining portion 14. A rib 22 is provided on the rear surface 21 of the retaining portion 14 extending over the base portion of the blade portion 12 as shown in FIG. 7, on the rear surface 21 of the retaining portion 14, a pin hole 26 is formed at the portion where the rib 22 is provided. As shown in FIG. 4, on the facing surface 15 of the blade portion 14 a spacer receiving hole 30 for inserting a spacer 28 (FIG. 3) is provided. On both sides of the base portion of the retaining portion 14 are provided engaging holes 32.

The edges of the metal plate which is bent such as to have an arcuate cross section and which constitutes the blade portion 12 are approximately parallel to the facing surface 15 of the retaining portion 14, and these edges constitute cutting edges 34 of the replaceable blade 10. The edges of the metal plate constituting the cutting edges 34 are slightly higher than the facing surface 15 of the retaining portion 14.

Figure 6:
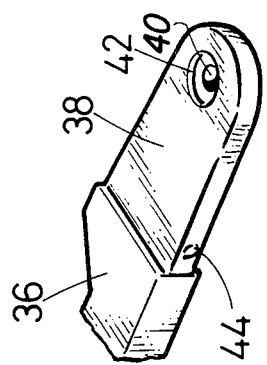
FIG. 6 is a perspective view of an insertion piece 38 of the scissor body 36.

On the other hand, as shown in FIG. 6, at the end portion of the scissor body 36, there is provided an insertion piece 38 which is inserted into the retaining portion 14 (FIG. 7). At the end portion of the insertion piece 38, a pin hole 40 (FIG. 6) is formed. Spacer receiving holes 42 are provided concentrically with respect to the pin hole 40 on the facing surfaces of both insertion pieces 38 of the pair of scissor bodies 36. On both side surfaces of the end portion of the insertion piece 38, protrusions 44 for engaging the engaging holes 32 (FIGS. 3 and 4) are provided so as to prevent the retaining portion 14 of the replaceable blade 10 from slipping off the insertion piece 38 of the scissor body 36.

When the replaceable blade 10 is mounted on the scissor body 36, the end portion of the scissor body 36 is held with one hand and the blade portion 12 of the replaceable blade 10 is held with the other hand. In this state, if the insertion piece 38 of the scissor body 36 is inserted firmly into the retaining portion 14 of the replaceable blade 10, the retaining portion 14 which increases in width toward the base portion, namely which has a tapering shape, is plastically deformed and expands slightly. Therefore, by the elastic contracting force of the metal plate which constitutes the retaining portion 41, the metal plate grasps the insertion piece 38 firmly, whereby the replaceable blade 10 is removably secured to the scissor body 36, and the engaging holes 32 engage with the protrusions 44, thereby preventing the retaining portion 14 of the replaceable blade 10 from slipping off the insertion piece 38 of the scissor body 36.

Figure 5:
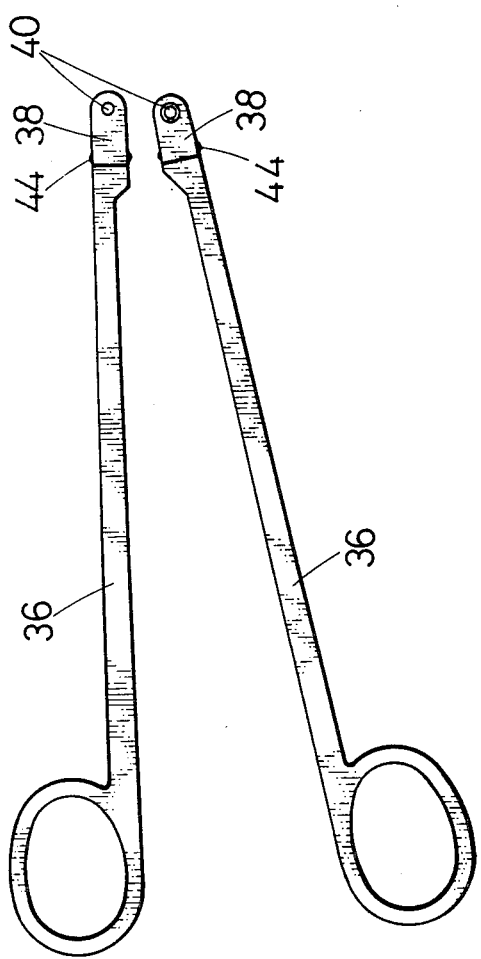
FIG. 5 is a plan view of a pair of scissor bodies 36.

The spacers 28 of FIG. 7 are next inserted, as shown in FIG. 6, into the spacer receiving holes 42 of the insertion pieces 38 of the pair of scissor bodies 36, and the pair of scissor bodies 36 of FIG. 5 are connected, as shown in FIG. 7, by means of the connecting pin 24 and the nut 46.

Figure 8:
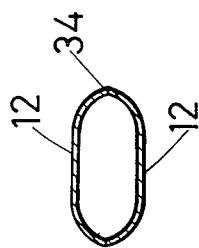
FIG. 8 is an enlarged sectional view taken along the line Y—Y of FIG. 2.

During use, since the spacers 28 directly come into contact with each other and as shown in FIG. 4 the facing surfaces 15 of the retaining portions 14 of the replaceable blades 10 are out of direct contact, there is a smooth sliding action at the connecting portion of the scissors. When the pair of scissor bodies 36 are connected, as is shown in FIG. 8, the edges of the metal plates constituting the blade portions 12 come into contact with each other and function as the cutting edges 34.

In the case of replacing the replaceable blade 10 of FIG. 4 the connecting pin 24 shown in FIG. 3 is removed, and the blade portion 12 of the replaceable blade 10 is firmly pulled with one hand while the end portion of the scissor body 36 shown in FIG. 3 is held fast with the other hand. Thus the engagement of the engaging holes 32 with the protrusions 44 is released and the replaceable blade 10 of FIG. 4 is pulled off.

In the first embodiment which has a structure in which the connecting pin 24 of FIG. 3 is provided as shown in FIG. 4 at the retaining portion 14 of the replaceable blade 10, the length of the replaceable blade 10 can advantageously be made long.

FIGS. 9 and 10 show a second embodiment of the invention.

In the second embodiment of replaceable blade type medical scissors, a connecting pin is not provided at the retaining portion of the replaceable blade. In the description of this embodiment like reference numerals denote like elements and only those features which are different from the first embodiment will be explained. A replaceable blade 48 has a structure similar to the replaceable blade 10 of the first embodiment except that it is devoid of the spacer receiving hole 30. One pair of scissor bodies 36 are connected by the connecting pin 24 and are not parted from each other when the replaceable blade 48 is replaced.

In the same way as in the first embodiment, an insertion piece 51 of the scissor body 36 is inserted into a retaining portion 50 of the replaceable blade 48. The retaining portion 50 is slightly expanded by plastic deformation, and the replaceable blade 48 is removably secured to the scissor body 36. Engaging holes 52 formed on the retaining portion 50 engage with the protrusions 44 provided on the insertion piece 51 and prevent the retaining portion 50 of the replaceable blade 48 from slipping off the insertion piece 51 of the scissor body 36. In the state where the replaceable blades 48 are secured to the scissor bodies 36, the edges of the metal plates constituting the blade portions 54 of the replaceable blades 48 come into contact with each other and function as the cutting edges 56 of the replaceable blade 48.

The edges 58 of the metal plate situated on the side of facing surface 49 of the retaining portion 50 are slightly inclined in the lengthwise direction of the replaceable blade 48, which eliminates the possibility of the edges 58, which come into contact with each other during use, interfering with each other and impeding the smooth sliding action of the scissors. In FIG. 10, a rib 60 provided on the rear surface of the base portion of the replaceable blade 48.

The second embodiment is advantageous in that, since the connecting pin 24 of FIG. 9 is not provided on the retaining portion 50 of FIG. 10, it is not necessary to remove the connecting pin 24 at the time of replacement of the replaceable blade 48.

A third embodiment of replaceable blade type medical scissors according to the invention is illustrated in FIGS. 11 and 12.

In the third embodiment, a connecting pin is provided at the retaining portion of a replaceable blade such that the connecting portions of the scissors enjoy a smooth sliding action without spacers.

As shown in FIG. 11, a replaceable blade 62 is composed of a blade portion 64 made of a metal plate bent in such a manner as to have an arcuate cross section, and a retaining portion 66 which is made of the metal plate bent into a envelope shape. The replaceable blade 62 is integrally provided at the base portion of the blade portion 64. The edges 68 of the metal plate situated on the side of the facing surface 67 of the retaining portion 66 oppose each other with a relatively wide space between them, and are arranged in the lengthwise direction of the replaceable blade 62. The edges of the metal plate constituting the blade portion 64 are approximately parallel to and slightly higher than the facing surface 67 of the retaining portion 66. Notches 70 are formed at the portion connecting the blade portion 64 and the retaining portion 66 so that the retaining portion 66 is easy to plastically deform. On the rear surface 71 of the retaining portion 66, a reinforcing rib 72 is protrudingly provided, and a pin hole 74 for receiving the connecting pin 24 of FIG. 12 is formed on the rib 72. An engaging hole 76 is formed on the rear surface 71 of the base portion of the retaining portion 66.

On the other hand, on both sides of an insertion piece 78 provided at the end portion of the scissor body 36 of FIG. 11, there are formed steppd portions 80, and at the end portion of the insertion piece 78, there is formed a pin hole 82. The height of the stepped portions 80 is greater than the thickness of the metal plate constituting the retaining portion 66. The facing surfaces of the insertion pieces 78 serve as sliding surfaces 84 for the scissors.

In the same way as in the first and second embodiments of the replaceable blade type medical scissors, when the insertion piece 78 of the scissor body 36 is inserted into the retaining portion 66 of the replaceable blade 62, the replaceable blade 62 is removably secured to the scissor body 36 and the engaging hole 76 provided on the replaceable blade 62 is engaged with a protrusion (not shown) provided on the scissor body 36, thereby preventing the retaining portion 66 of the replaceable blade 62 from slipping off the insertion piece 78 of the scissor body 36. When one pair of the scissor bodies 36 is connected as shown in FIG. 12 by the connecting pin 24 and the nut 46, the wide area of the sliding surfaces 84 shown in FIG. 11 for the insertion pieces 78 allows a smooth sliding action at the connecting portion of the scissors and thus enables a stable cutting operation. When the pair of scissor bodies 36 are connected, the edges of the metal plates constituting the blade portions 64 of the replaceable blades 62 come into contact with each other and function as the cutting edges 86 of the replaceable blades 62.

In all the embodiments, the arcuate cross section of the blade portion of the replaceable blade increases the cutting strength of the blade in cooperation with the rib which is protrudingly provided on the retaining portion. It is also possible to use the scissors with a resin charged into the depressed portions of the blade portions.

As described above, according to the invention, the blade portions of medical scissors are made replaceable and thus only the replaceable blades need to be thrown away, which dispenses with the need for sterilization and reassembly of the scissors after use, which task has been considered troublesome, and enables a consistent cutting operation of a good quality by renewing the replaceable blades. Furthermore, since an appropriate specific blade selected from among the various kinds of replaceable blades of different sizes and shapes which are prepared in advance is mounted on the scissor body, the scissor bodies are interchangeable, and thus the number of the scissor bodies required to be prepared can be decreased remarkably, which results in a very easy handling of scissors.

In addition, the structure wherein the metal plate constituting the retaining portion of the replaceable blade is plastically deformed and having an elastic contracting force by which the metal plate of the replaceable blade is secured to the scissor body securely attaches the blade to the scissor body and greatly facilitates frequent replacement of the blade.

What is claimed is:

1. Exchangeable blade type medical scissors comprising:
   a pair of scissors bodies;
   a pair of replaceable blades each of which is composed of a blade portion made of a metal plate which is bent such as to have an arcuate cross section, and a retaining portion which is constituted by said metal plate bent into an envelope form which gradually increases in width towards the base portion;
   notch means adapted to allow plastic deformation and integrally provided at the base portion of said blade portion;
   a pair of insertion pieces which are respectively provided at the end portion of each of said scissor bodies and each of which is inserted into said retaining portion of said replaceable blade such that said scissor body is removably secured to said replaceable blade by the elastic contracting force of said retaining portion;
   a connecting pin which connects said pair of scissor bodies at said retaining portions of said replaceable blades;
   protrusions provided on one of either of said retaining portions of said replaceable blades or said insertion pieces of said scissor bodies, and on the other, engaging holes provided so that said replaceable blades may be prevented from slipping off said scissor bodies by the engagement of said protrusions with said engaging holes when said replaceable blades are mounted on said scissor bodies; and
   reinforcing ribs provided on the retaining portions of said replaceable blades.

* * * * *